(12) United States Patent  
Ishihara

(10) Patent No.: US 9,259,192 B2
(45) Date of Patent: Feb. 16, 2016

(54) RADIATION TOMOGRAPHY APPARATUS, DOSE CALCULATION METHOD, AND PROGRAM

(71) Applicant: GE MEDICAL SYSTEMS GLOBAL TECHNOLOGY COMPANY, LLC, Waukesha, WI (US)

(72) Inventor: Yotaro Ishihara, Tokyo (JP)

(73) Assignee: General Electric Company, Schenectady, NY (US)

( * ) Notice: Subject to any disclaimer, the term of this patent is extended or adjusted under 35 U.S.C. 154(b) by 193 days.

(21) Appl. No.: 13/678,356

(22) Filed: Nov. 15, 2012

(65) Prior Publication Data

US 2013/0136227 A1 May 30, 2013

(30) Foreign Application Priority Data

Nov. 29, 2011 (JP) .................... 2011-260480

(51) Int. Cl.
*A61B 6/00* (2006.01)
*A61B 6/03* (2006.01)
*G01T 1/169* (2006.01)

(52) U.S. Cl.
CPC .............. *A61B 6/032* (2013.01); *A61B 6/461* (2013.01); *A61B 6/542* (2013.01); *A61B 6/583* (2013.01); *G01T 1/169* (2013.01); *A61B 6/56* (2013.01)

(58) Field of Classification Search
USPC .................................. 378/1, 4, 18
See application file for complete search history.

(56) References Cited

U.S. PATENT DOCUMENTS

| 5,511,107 | A | 4/1996 | Sliski |
| 5,635,709 | A | 6/1997 | Sliski et al. |
| 6,636,622 | B2 | 10/2003 | Mackie et al. |
| 6,714,620 | B2 | 3/2004 | Caflisch et al. |
| 7,605,365 | B2 | 10/2009 | Chen et al. |
| 7,842,929 | B2 | 11/2010 | Krautim et al. |
| 8,110,811 | B2 | 2/2012 | Krautim et al. |
| 8,173,968 | B1 | 5/2012 | Nelms |
| 8,227,762 | B2 | 7/2012 | Krautim et al. |
| 2011/0278443 | A1 | 11/2011 | Mizuta et al. |

FOREIGN PATENT DOCUMENTS

| JP | 2004195121 A | 7/2004 |
| JP | 2007054372 | 3/2007 |
| JP | 2007054372 A | 3/2007 |
| JP | 2009042247 A | 2/2009 |

OTHER PUBLICATIONS

International Electrotechnical Commission (IEC), Medical Electrical Equipment, IEC 60601-1-3, Edition 2.0, Jan. 2008.
Kanae Nishizawa, "Special Report 1: CT Scan Manual for Chest CT Diagnostic Check", Medicinal Physics Department, National Institute of Radiological Sciences, undated, 3 pages (English Translation).

*Primary Examiner* — Nicole Ippolito
*Assistant Examiner* — Hanway Chang
(74) *Attorney, Agent, or Firm* — Lucas Divine; General Electric Company

(57) ABSTRACT

A radiation tomography apparatus is provided. The radiation tomography apparatus is configured to display a dose near a surface of a subject.

13 Claims, 10 Drawing Sheets

FIG. 3

| FIRST TABLE (CONVENTIONAL REFERENCE DOSE) | | | ~T1 |
|---|---|---|---|
| | PHANTOM TYPE (SIZE) | | |
| | HEAD (16cm in diameter) | BODY (32cm in diameter) | |
| TUBE VOLTAGE — 80kV | conv_ref_Dose (h,80) | conv_ref_Dose (b,80) | |
| 100kV | conv_ref_Dose (h,100) | conv_ref_Dose (b,100) | |
| 120kV | conv_ref_Dose (h,120) | conv_ref_Dose (b,120) | |
| 140kV | conv_ref_Dose (h,140) | conv_ref_Dose (b,140) | |

| SECOND TABLE (BODY SURFACE REFERENCE DOSE) | | | ~T2 |
|---|---|---|---|
| | PHANTOM TYPE (SIZE) | | |
| | HEAD (16cm in diameter) | BODY (32cm in diameter) | |
| TUBE VOLTAGE — 80kV | skin_ref_Dose (h,80) | skin_ref_Dose (b,80) | |
| 100kV | skin_ref_Dose (h,100) | skin_ref_Dose (b,100) | |
| 120kV | skin_ref_Dose (h,120) | skin_ref_Dose (b,120) | |
| 140kV | skin_ref_Dose (h,140) | skin_ref_Dose (b,140) | |

RADIATION TOMOGRAPHY APPARATUS, DOSE CALCULATION METHOD, AND PROGRAM

CROSS REFERENCE TO RELATED APPLICATIONS

This application claims the benefit of Japanese Patent Application No. 2011-260480 filed Nov. 29, 2011, which is hereby incorporated by reference in its entirety.

BACKGROUND OF THE INVENTION

The present invention relates to a radiation tomography apparatus, a dose calculation method, and a program thereof.

A radiation tomography apparatus such as an X-ray CT (Computed Tomography) scanner is configured to display a CTDI value indicative of a dose per unit slice thickness or a DLP value indicative of a dose per examination as a whole (e.g., see FIG. 27 in Japanese Patent Application Publication No. 2007-54372). This enables evaluating radiation exposure of a subject.

Actually, however, the dose variance is uneven. The dose variance is maximized on the surface of an imaging portion and decreases toward the center thereof. Highly radiation-sensitive portions exist near the body surface of a subject.

As the related art practices, using only the CTDI value indicative of a dose per unit slice thickness or the DLP value indicative of a dose per examination as a whole cannot accurately evaluate the radiation exposure on a subject.

In consideration of this, there is an increasing demand for a technology that provides information capable of more accurately evaluating radiation exposure on a subject.

BRIEF DESCRIPTION OF THE INVENTION

According to a first aspect, a radiation tomography apparatus that displays a dose near a surface of a subject is provided.

According to a second aspect, the radiation tomography apparatus of the first aspect is provided. The radiation tomography apparatus includes a calculation means that calculates the dose based on a radiation dose measured only at a measurement position near a surface of a phantom that is irradiated.

According to a third aspect, the radiation tomography apparatus of the second aspect is provided, wherein the calculation means calculates the dose based on a radiation dose measured at a measurement position near a surface of the phantom where the radiation dose is practically maximum when the phantom is irradiated.

According to a fourth aspect, the radiation tomography apparatus of the third aspect is provided, wherein the phantom is placed on a scanning table plate, and wherein the position where the radiation dose is practically maximum is a position which a radiation source is most approximated.

According to a fifth aspect, the radiation tomography apparatus of any one of the second to the fourth aspects is provided, wherein the calculation means calculates the dose based on a first radiation dose measured at the measurement position near the surface when a scan of the phantom is performed.

According to a sixth aspect, the radiation tomography apparatus of any one of the second to the fourth aspects is provided, wherein the calculation means calculates the dose based on a first radiation dose that results from dividing a radiation dose measured at the measurement position near the surface when a scan of the phantom is performed by a profile area resulting from normalizing a dose profile in a radiation beam width direction according to its peak dose value, the dose profile being measured at the measurement position when the phantom is irradiated with the same radiation beam width as for the scan.

According to a seventh aspect, the radiation tomography apparatus of the sixth aspect is provided, wherein the dose profile results from averaging a plurality of dose profiles measured by positioning a radiation source for irradiation at a plurality of different view angles.

According to an eighth aspect, the radiation tomography apparatus of any one of the fifth to the seventh aspects is provided, wherein the calculation means calculates the dose based on a radiation dose resulting from dividing the first radiation dose by a helical pitch when helical scan is specified as a desired scan condition.

According to a ninth aspect, the radiation tomography apparatus of any one of the fifth to the seventh aspects is provided, wherein the calculation means calculates the dose based on a radiation dose resulting from dividing the first radiation dose by a helical pitch equivalent according to time-weighted average when variable-pitch helical scan is specified as a desired scan condition.

According to a tenth aspect, the radiation tomography apparatus of any one of the fifth to the ninth aspects is provided, wherein the calculation means calculates the dose based on a view angle range for performing a partial scan that irradiates for less than 360 degrees, when the partial scan is specified as a desired scan condition.

According to an eleventh aspect, the radiation tomography apparatus of any one of the fifth to the ninth aspects is provided, wherein the calculation means calculates the dose based on the first radiation dose obtained by performing a partial scan as the scan of the phantom, when the partial scan that irradiates for less than 360 degrees is specified as a desired scan condition.

According to a twelfth aspect, the radiation tomography apparatus of any one of the fifth to the ninth aspects is provided, wherein the calculation means calculates the dose based on a radiation dose resulting from averaging a plurality of the first radiation doses obtained by performing a partial scan for a plurality of view angles ranges different from each other as the scan for the phantom, when the partial scan that irradiates for less than 360 degrees is specified as a desired scan condition.

According to a thirteenth aspect, the radiation tomography apparatus of any one of the fifth to the ninth aspects is provided, wherein full scan to deliver radiation 360 degrees is performed on the phantom.

According to a fourteenth aspect, the radiation tomography apparatus of any one of the second to the thirteenth aspects is provided, wherein the phantom is acrylic and is shaped to be columnar one of 16 cm and 32 cm in diameter and wherein a measurement position near the surface is deep at least 0.5 cm and up to 2.0 cm from the surface.

According to a fifteenth aspect, a dose calculation method is provided. The dose calculation method includes calculating a dose for a subject imaged by a radiation tomography apparatus based on a radiation dose measured only at a measurement position near a surface of an irradiated phantom.

According to a sixteenth aspect, the dose calculation method of the fifteenth aspect is provided, wherein the method measures a first radiation dose at the measurement position near the surface for scanning on the phantom and calculates the dose based on the first radiation dose.

According to a seventeenth aspect, the dose calculation method of the fifteenth aspect is provided, wherein the method measures the radiation dose at the measurement position near the surface when a scan of the phantom is performed and a profile area of a dose profile in a radiation beam width direction normalized according to its peak dose value at the measurement position when the phantom is irradiated with the same radiation beam width as for the scan and calculates the dose based on a first radiation dose resulting from dividing said radiation dose at the measurement position near the surface by said profile area.

According to an eighteenth aspect, a program is provided. The program allows a computer to function as a calculation means that calculates a dose for a subject imaged by a radiation tomography apparatus, based on a radiation dose measured only at a measurement position near a surface of a phantom when the phantom is irradiated.

According to a nineteenth aspect, the program of the eighteenth aspect is provided, wherein the calculation means calculates the dose based on a first radiation dose measured at the measurement position near the surface when a scan of the phantom is performed.

According to a twentieth aspect, the program of the eighteenth aspect is provided, wherein the calculation means calculates the dose based on a first radiation dose that results from dividing a radiation dose measured at the measurement position near the surface when a scan of the phantom is performed by a profile area resulting from normalizing a dose profile in a radiation beam width direction according to its peak dose value, the dose profile being measured at the measurement position when the phantom is irradiated with the same radiation beam width as for the scan.

According to the above-mentioned aspects, it is possible to calculate a dose virtually maximized near the surface of a subject and provide information capable of accurately evaluating the radiation exposure on the subject.

BRIEF DESCRIPTION OF THE DRAWINGS

FIG. 3 shows first and second tables stored in a dose calculation portion;

DETAILED DESCRIPTION OF THE INVENTION

Exemplary embodiments will be described below.

First Embodiment

Figure 1:
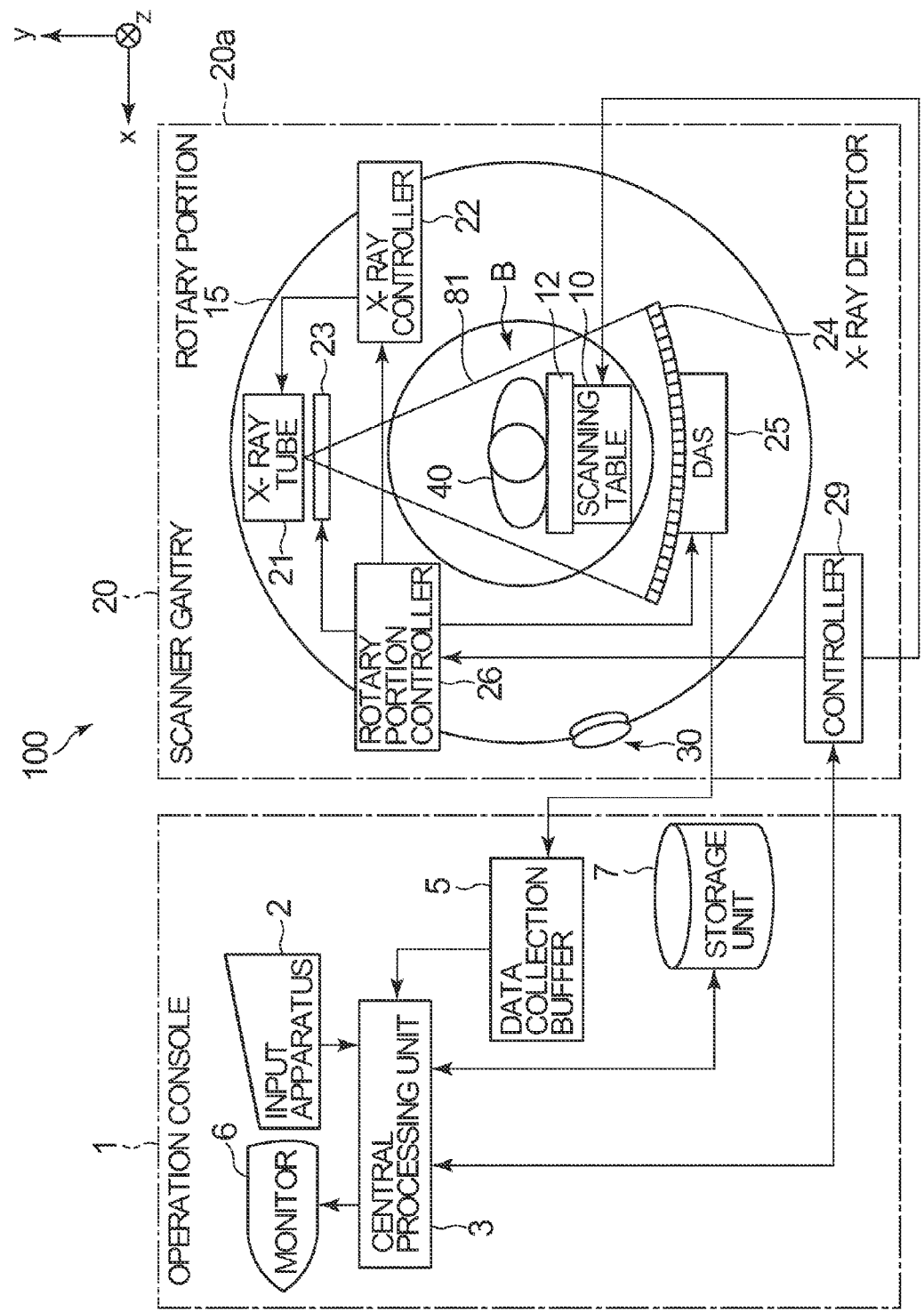
FIG. 1 schematically shows a configuration of an X-ray CT scanner according to an embodiment.

FIG. 1 schematically shows a configuration of an X-ray CT scanner according to the embodiment. An X-ray CT scanner 100 includes an operation console 1, a scanning table 10, and a scanner gantry 20.

The operation console 1 includes an input apparatus 2, a central processing unit 3, a data collection buffer 5, a monitor 6, and a storage unit 7. The input apparatus 2 accepts input from an operator. The central processing unit 3 controls components for imaging a subject and processes data for generating an image. The data collection buffer 5 collects data acquired from the scanner gantry 20. The monitor 6 displays an image. The storage unit 7 stores a program and data.

The scanning table 10 includes a cradle 12 that mounts a subject 40 and conveys it to an opening of the scanner gantry 20. A motor contained in the scanning table 10 vertically and horizontally moves the cradle 12. The following description defines the z direction as a body axis direction of the subject 40, that is, a linear movement direction of the cradle 12, the y direction as a vertical direction, and the x direction as a horizontal direction perpendicular to the z direction and the y direction.

The scanner gantry 20 includes a rotary portion 15 and a body portion 20a that rotatably supports the rotary portion 15. The rotary portion 15 includes an X-ray tube 21, an X-ray controller 22, a collimator 23, an X-ray detector 24, a data acquisition system (DAS) 25, and a rotary portion controller 26. The X-ray controller 22 controls the X-ray tube 21. The collimator 23 collimates an X-ray beam 81 generated from the X-ray tube 21. The X-ray detector 24 detects the X-ray beam 81 that transmits through the subject 40. The DAS 25 collects output from the X-ray detector 24 by converting the output into projection data. The rotary portion controller 26 controls the X-ray controller 22, the collimator 23, and the DAS 25. The body portion 20a includes a controller 29 that exchanges control signals with the operation console 1 and the scanning table 10. The rotary portion 15 and the body portion 20a are electrically connected to each other via a slip ring 30.

Figure 2:
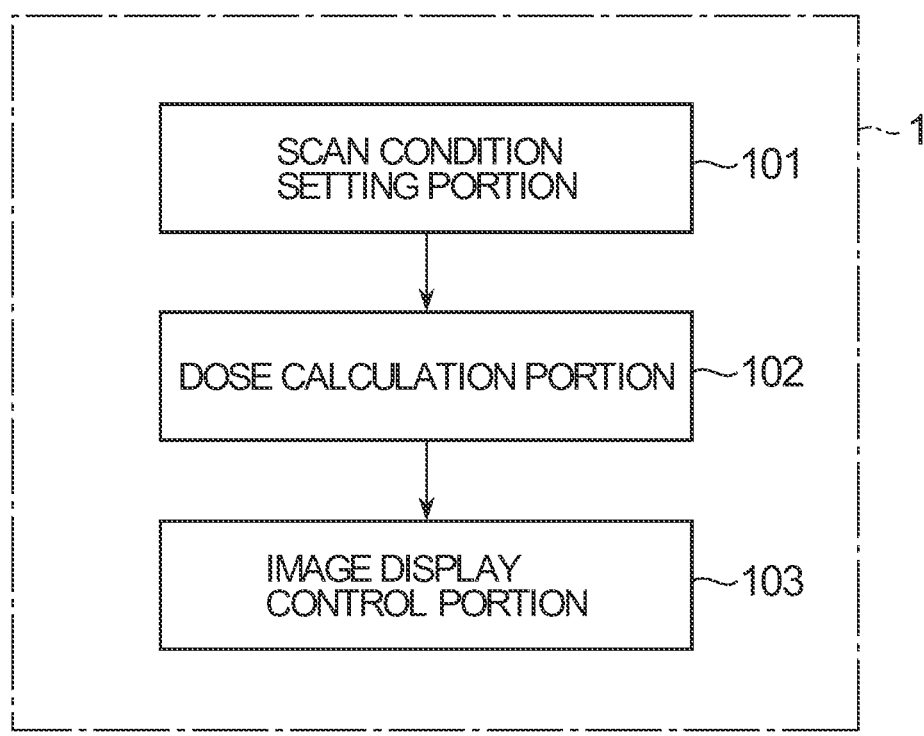
FIG. 2 is a function block diagram showing portions related to dose calculation performed in the X-ray CT scanner according to a first embodiment.

FIG. 2 is a function block diagram showing portions related to dose calculation performed in the X-ray CT scanner according to the first embodiment.

As shown in FIG. 2, the X-ray CT scanner according to the embodiment includes a scan condition setting portion 101, a dose calculation portion 102, and an image display control portion 103.

The scan condition setting portion 101 configures a specified scan condition used for the main scan in accordance with operator operations. The scan condition includes an imaging portion, a scan range, a tube voltage and a tube current for the X-ray tube, gantry rotation time for one rotation, and a scan mode. The scan condition also includes a helical pitch in helical mode if applicable as the scan mode as well as an index value for image noise if automatic exposure control is used. These scan conditions determine a setup dose real_mAs that is used to perform main scan on a subject and is expressed as a product of a setup tube voltage KV, the tube current, and the X-ray exposure time. The imaging portion is assumed to be selected from "head/infant" and "body," for example.

The dose calculation portion 102 calculates the dose for a subject based on the set desired scan condition. In the embodiment, the dose calculation portion 102 calculates four types of doses, that is, conventional CTDI value conv_CTDI, conventional DLP value conv_DLP, value skin_CTDI equivalent to body surface CTDI, and value skin_DLP equivalent to body surface DLP.

The following describes in detail a calculation process in the dose calculation portion 102.

The dose calculation portion 102 stores a first table T1 and a second table T2. The first table T1 relates to conventional reference dose conv_ref_Dose and is used to calculate conventional CTDI value conv_CTDI. The second table T2 relates to body surface standard dose skin_ref_Dose and is used to calculate value skin_CTDI equivalent to body surface CTDI.

FIG. 3 shows exemplary first and second tables.

Conventional reference dose conv_ref_Dose contained in the first table T1 indicates a CTDIw value acquired after a reference phantom is scanned under the scan condition of reference dose ref_mAs as a specified dose (mAs) while the X-ray tube is rotated one turn.

Figure 4A:
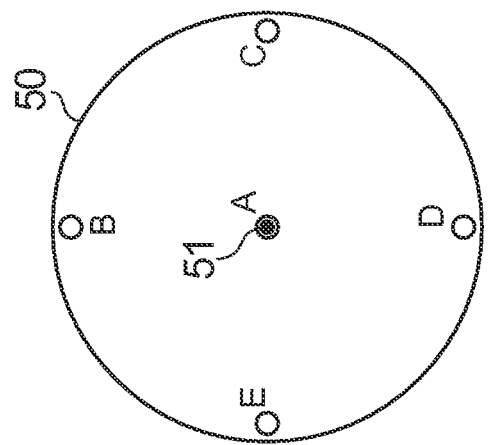
FIGS. 4A and 4B show an exemplary reference phantom and X-ray sensor.
Figure 4B:
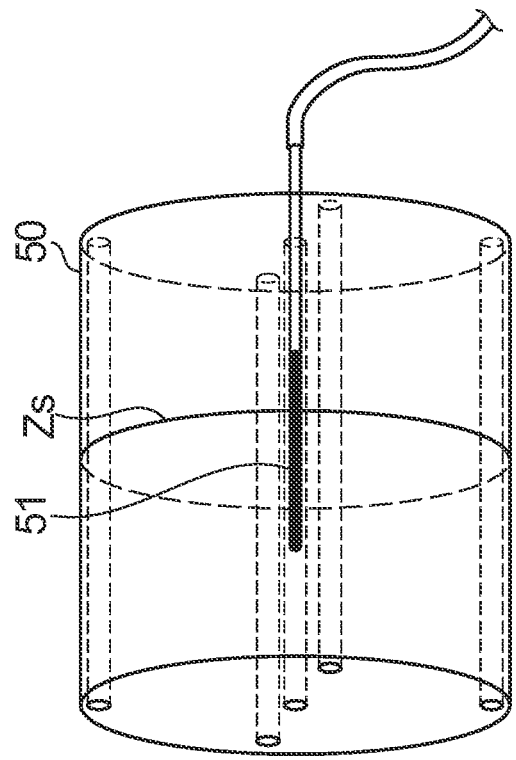

FIGS. 4A and 4B show an exemplary reference phantom and an X-ray sensor. FIG. 4A shows the reference phantom viewed in the axial direction. FIG. 4B is a perspective view. A reference phantom 50 is made of acrylics, for example, and has a columnar shape as shown in FIGS. 4A and 4B. The reference phantom 50 is provided with measurement holes corresponding to a center part A and deep parts B, C, D, and E near the surface along the cylindrical axis direction. The X-ray dose is measured to find a CTDIw value. Normally, for this purpose, a rod-shaped X-ray sensor 51 is inserted into the holes corresponding to the center part A and the deep parts B, C, D, and E in order to scan position Zs in the reference phantom 50. The X-ray sensor 51 is equivalent to an ionization chamber 100 mm long.

The reference phantom 50 may be available in two types, that is, a head phantom 16 cm in diameter and a body phantom 32 cm in diameter. The deep part may be positioned 0.5 cm or more and 2.0 cm or less from the surface of the reference phantom 50. The depth in at least some embodiments is 1 cm from the surface.

Conventional reference dose conv_ref_Dose, that is, the CTDIw value, can be found based on X-ray doses that are measured at the center and positions near the surface of the reference phantom 50. The following equation defines the CTDIw value.

$$\text{Conventional reference dose } conv\_ref\_Dose = CTDIw = \tfrac{1}{3}CTDI100,center + \tfrac{2}{3}CTDI100,edge,ave \qquad \text{Equation 1}$$

In this equation, CTDI100,center denotes the X-ray dose per unit slice thickness and is measured when the rod-shaped X-ray sensor 51 is inserted into the center part A of the reference phantom 50. CTDI100,edge,ave denotes the average X-ray dose per unit slice thickness and is measured when the rod-shaped X-ray sensor 51 is inserted into the deep parts B, C, D, and E as measurement positions near the surface of the reference phantom 50.

As shown in FIG. 3, the first table T1 shows the conventional reference dose conv_ref_Dose corresponding to the type or size of the reference phantom under the condition of the tube voltage used to scan the reference phantom 50.

The body surface reference dose skin_ref_Dose is equivalent to the CTDI value corresponding to the vicinity of the surface of the reference phantom 50. The body surface reference dose skin_ref_Dose is acquired when the reference phantom 50 is scanned for one turn of the X-ray tube under the scan condition of reference dose ref_mAs as the dose (mAs).

The X-ray dose is measured to find the body surface reference dose skin_ref_Dose. For this purpose, the rod-shaped X-ray sensor 51 is inserted into the deep part hole as the measurement position near the surface of the reference phantom 50 to scan the reference phantom.

The body surface reference dose skin_ref_Dose shown in the second table T2 is found based on the X-ray dose measured "only" at the measurement position near the surface of the reference phantom 50. In this embodiment, the following equation defines the body surface reference dose skin_ref_Dose.

$$\text{Body surface reference dose } skin\_ref\_Dose = CTDI100, edge \qquad \text{Equation 2}$$

In this equation, CTDI100,edge denotes the X-ray dose that is measured at the deep part as the measurement position near the surface of the reference phantom 50 using the rod-shaped X-ray sensor 51 as an ionization chamber 100 mm long. In this embodiment, CTDI100,edge corresponds to a measurement position near the surface of the reference phantom 50 and is measured at the position capable of virtually maximizing the X-ray dose to be measured.

Figure 5:
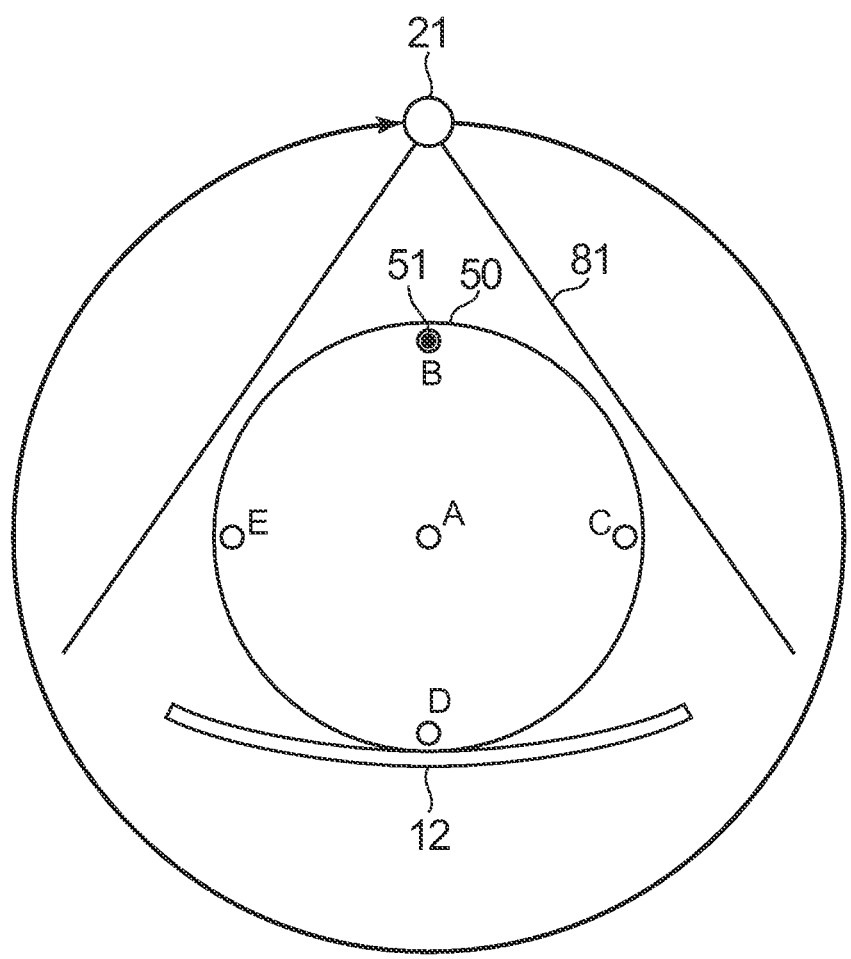
FIG. 5 illustrates full scan performed on a subject placed on a cradle.

As shown in FIG. 5, for example, an X-ray 81 passes through the cradle 12 and thereby decreases its intensity when the reference phantom 50 is placed on the cradle 12 for scanning. To correctly measure the X-ray, the X-ray sensor 51 is inserted into a position nearest to the X-ray tube 21, that is, into the deep part B corresponding to the topmost measurement position of the reference phantom 50. This enables finding the maximum of doses near the surface of the reference phantom 50 as the value skin_CTDI equivalent to body surface CTDI and facilitates preventing underestimation of the radiation exposure on a subject.

As shown in FIG. 3, the second table T2 shows the body surface reference dose skin_ref_Dose corresponding to the type (size) of the reference phantom 50 under the condition of the tube voltage used to scan the reference phantom 50.

As described above, the dose calculation portion 102 stores the reference dose corresponding to the tube voltage, the reference phantom type, and the X-ray dose measurement location (the center and the surface or only the surface) while the reference dose is found through scanning the reference phantom 50 under the scan condition of reference dose ref_mAs as a dose (mAs).

The dose calculation portion 102 specifies a condition that is registered in the first table T1 and the second table T2 and combines the tube voltage equal to or most approximate to the setup tube voltage set_KV with the type (size) of the reference phantom approximate to a setup imaging portion set_obj. The dose calculation portion 102 references the first table T1 and reads the conventional reference dose conv_ref_Dose corresponding to the specified condition. The dose calculation portion 102 multiplies the read conventional reference dose conv_ref_Dose by a factor represented as (setup dose set_mAs/reference dose ref_mAs) to calculate the conventional CTDI value conv_CTDI.

$$\text{Conventional } CTDI \text{ value } conv\_CTD = conv\_ref\_Dose \cdot (set\_mAs/ref\_mAs) \qquad \text{Equation 3}$$

The dose calculation portion 102 references the second table T2 and reads the body surface reference dose skin_ref_Dose corresponding to the specified condition. The dose calculation portion 102 multiplies the read-out conventional reference dose skin_ref_Dose by a factor represented as (setup dose set_mAs/reference dose ref_mAs) to calculate the value skin_CTDI equivalent to body surface CTDI.

$$\text{Value } skin\_CTDI \text{ equivalent to body surface } CTDI = skin\_ref\_Dose \cdot (set\_mAs/ref\_mAs) \qquad \text{Equation 4}$$

If helical mode is enabled as the scan mode, the dose calculation portion 102 divides the values calculated by Equations 3 and 4 by helical pitch hp to find the conventional CTDI value conv_CTDI and the value skin_CTDI equivalent to body surface CTDI, respectively. The helical pitch hp represents the ratio between a relative movement distance and an X-ray beam width when the X-ray tube 21 rotates one turn around a subject. If variable-pitch helical mode is enabled as the scan mode, the dose calculation portion 102 further divides the values calculated by Equations 3 and 4 by helical pitch equivalent hp' based on time-weighted addition to find the conventional CTDI value conv_CTDI and the value skin_CTDI equivalent to body surface CTDI respectively.

The dose calculation portion 102 multiplies the conventional CTDI value conv_CTDI and the value skin_CTDI equivalent to body surface CTDI calculated above by a predetermined scan range width L to find the conventional DLP value conv_DLP and the value skin_DLP equivalent to body surface DLP, respectively.

The image display control portion 103 controls the monitor 6 so as to display various types of images and information on a screen as needed. According to the embodiment, the image display control portion 103 allows the screen of the monitor 6 to display the dose calculated by the dose calculation portion 102.

The following describes operations in the X-ray CT scanner according to the embodiment.

Figure 6:
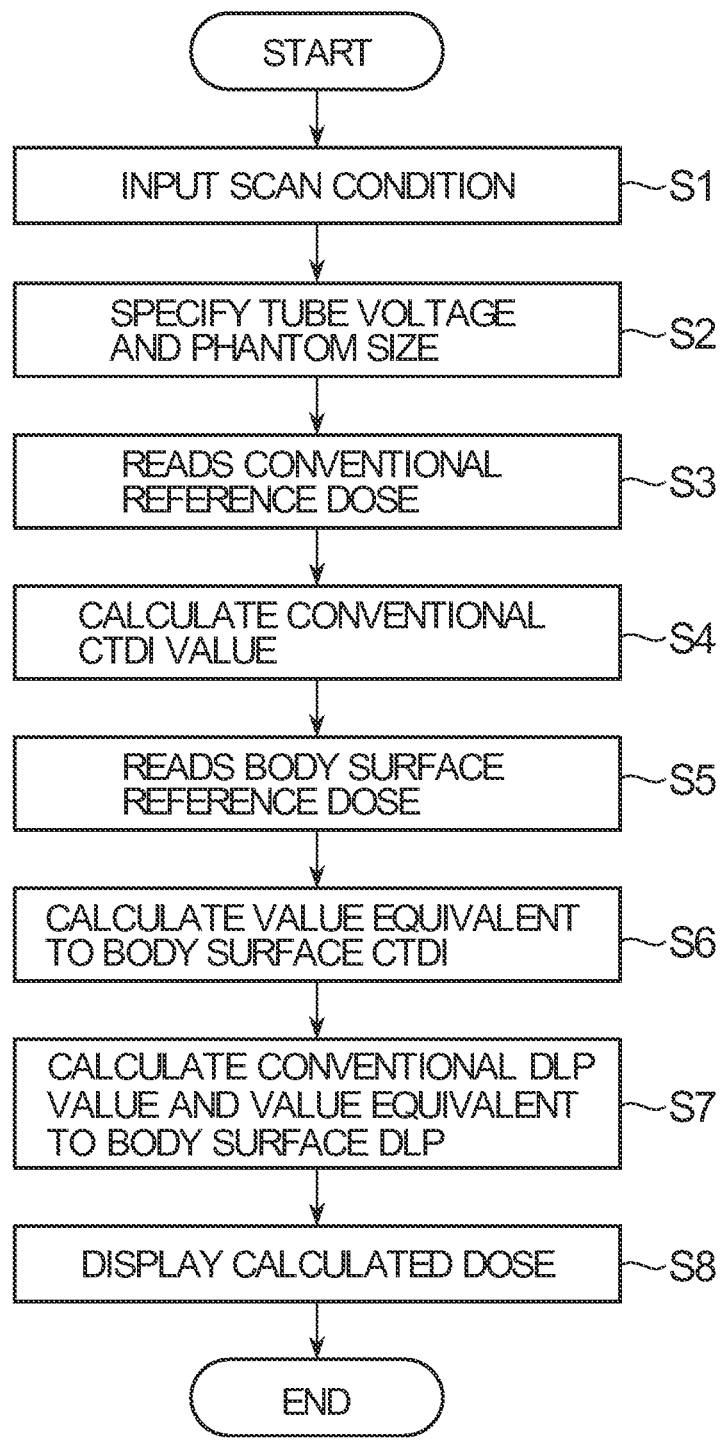
FIG. 6 is a flowchart showing a flow of dose calculation in the X-ray CT scanner according to the first embodiment.

FIG. 6 is a flowchart showing a flow of dose calculation in the X-ray CT scanner according to the embodiment.

At step S1, an operator inputs a scan condition while referencing the previously acquired scout image of a subject. The scan condition setting portion 101 configures the input scan condition as a scan condition for the main scan. The configured scan condition contains an imaging portion, a scan range, a tube voltage and a tube current for the X-ray tube, and scan mode. As a result, the setup tube voltage set_KV and the setup dose set_mAs are settled.

At step S2, the dose calculation portion 102 specifies a condition that combines a tube voltage equal to or most approximate to the setup tube voltage set_KV with the type (size) of a reference phantom sized approximately to the setup imaging portion set_obj.

At step S3, the dose calculation portion 102 references the first table T1 and reads the conventional reference dose conv_ref_Dse corresponding to the specified condition.

At step S4, the dose calculation portion 102 multiplies the read conventional reference dose conv_ref_Dose by a factor represented as (setup dose set_mAs/reference dose ref_mAs) to calculate the conventional CTDI value conv_CTDI. If helical mode or variable-pitch helical mode is enabled as the scan mode, the calculation takes into consideration the helical pitch hp or the helical pitch equivalent hp'.

At step S5, the dose calculation portion 102 references the second table T2 and reads the body surface reference dose skin_ref_Dose corresponding to the specified condition.

At step S6, the dose calculation portion 102 multiplies the read body surface reference dose skin_ref_Dose by a factor represented as (setup dose set_mAs/reference dose ref_mAs) to calculate the value skin_CTDI equivalent to body surface CTDI. If helical mode or variable-pitch helical mode is enabled as the scan mode, the calculation takes into consideration the helical pitch hp or the helical pitch equivalent hp'.

At step S7, the dose calculation portion 102 multiplies the conventional CTDI value conv_CTDI and the value skin_CTDI equivalent to body surface CTDI calculated above by the predetermined scan range width L to find the conventional DLP value conv_DLP and the value skin_DLP equivalent to body surface DLP, respectively.

At step S8, the image display control portion 103 allows the screen of the monitor 6 to display the dose calculated by the dose calculation portion 102.

Figure 7:
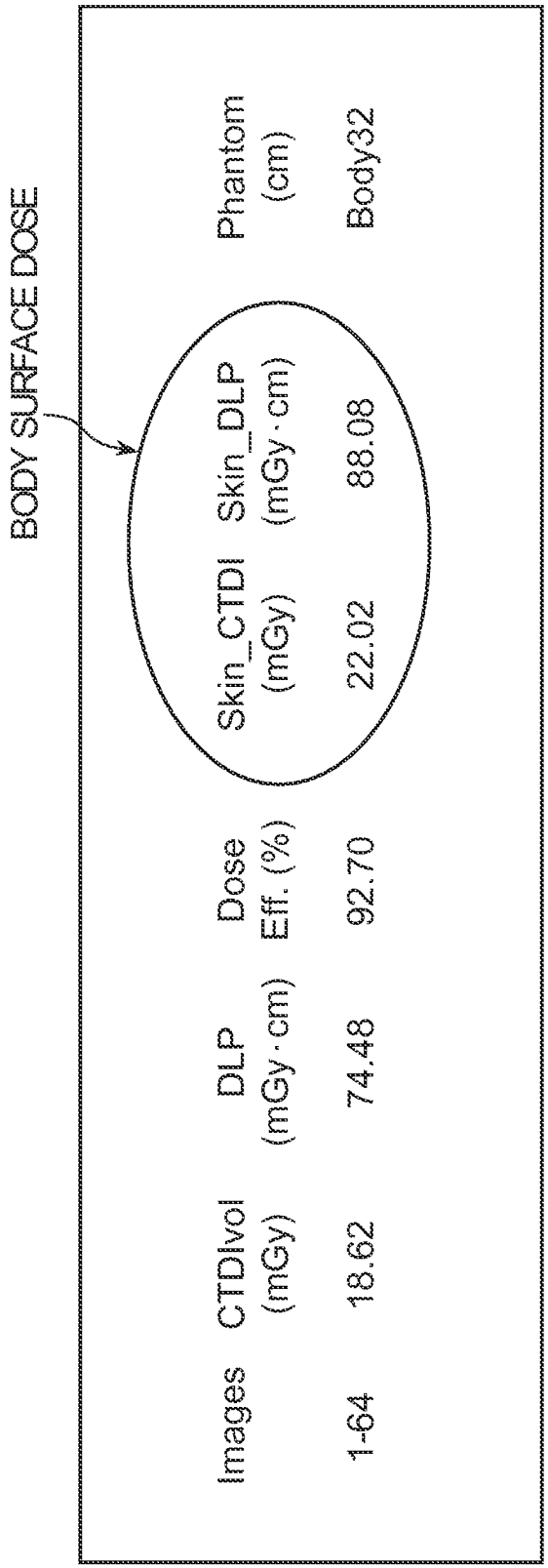
FIG. 7 shows an exemplary display of a calculated dose.

FIG. 7 shows an exemplary display of a calculated dose.

According to the first embodiment, it is possible to calculate a dose virtually maximized on the surface or its vicinity of a subject and provide information capable of accurately evaluating the radiation exposure on the subject.

International Electro technical Commission (IEC) 60601 specifies the existing method of providing doses, but does not prescribe the provision of information about a dose corresponding to the subject surface.

However, the dose corresponding to the subject surface represents practically the maximum dose for a subject as well as the dose corresponding to a position where a portion sensitive to radiation exists. Accordingly, the embodiment provides the dose information very advantageous to evaluation of the radiation exposure on a subject.

Second Embodiment

The first embodiment calculates the value skin_CTDI equivalent to body surface CTDI using the X-ray dose that is measured using the rod-shaped X-ray sensor as an ionization chamber 100 mm long. In this case, the calculated dose is averaged in the z direction and does not take into consideration the variance in the z direction.

The second embodiment takes into consideration the variance of doses in two directions and accurately calculates the maximum dose that belongs to doses near the surface of the reference phantom 50 and is available as a value equivalent to the body surface CTDI.

Generally, a rod-shaped X-ray sensor using an ionization chamber 100 mm long (e.g., radiation monitor Radcal® 9015 manufactured by RadCal—Radcal® is a registered trademark of Radcal corporation, of Monrovia, Calif.) outputs highly accurate dose values but measures with difficulty the variance of doses in the z direction. On the other hand, a small-sized semiconductor X-ray sensor (e.g., X-ray analyzer Barracuda manufactured by RTI) outputs less accurate dose values but excels in the linearity of doses and is suitable for measuring the variance of doses in the z direction.

The embodiment utilizes the advantages of these X-ray sensors and defines the body surface reference dose skin_ref_Dose as follows.

The X-ray tube rotates one turn to scan the reference phantom 50 under the scan condition of the reference dose ref_mAs as a dose (mAs) and measures X-ray dose V at a measurement position near the surface of the reference phantom 50. To measure the X-ray dose V, the rod-shaped X-ray sensor 51 using the ionization chamber 100 mm long is inserted into the deep part B as the topmost measurement position of the reference phantom 50.

The X-ray irradiation is performed with the same X-ray beam width as the scan in order to find a maximum dose value in the z direction. Dose profile PF in the z direction is measured at the same position as the measurement position near the surface.

Figure 8:
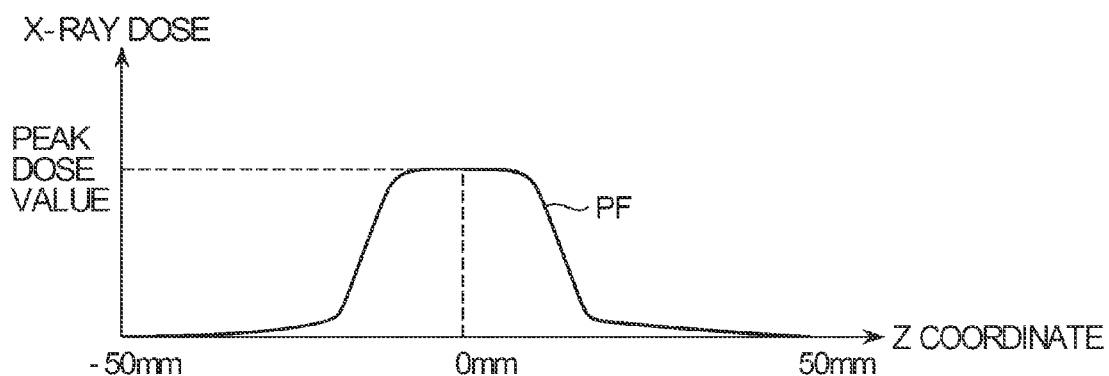
FIG. 8 shows an exemplary dose profile.

For example, a small-sized semiconductor sensor for dose measurement is inserted into the deep part B as a measurement position near the surface of the reference phantom 50. The reference phantom 50 is then placed on the cradle 12. The X-ray tube 21 is positioned at view angle 0 degrees, that is, topmost. The cradle 12 is gradually moved in the z direction. The X-ray tube 21 irradiates an X-ray beam to the reference phantom 50 to sample an output from the semiconductor sensor. Sampled values are plotted in graph form using the z direction as the horizontal axis. As a result, the dose profile PF shown in FIG. 8 is found.

To find the accurate dose profile PF, a sampling interval in the z direction needs to be sufficiently decreased up to 0.5 mm, for example. The dose profile PF is measured ±5 cm in the z direction from the X-ray beam center, that is, a total of 10 cm, for example.

The dose profile PF may result from averaging dose profiles measured in the above-mentioned method while the X-ray tube 21 is changed to different view angles.

Figure 9:
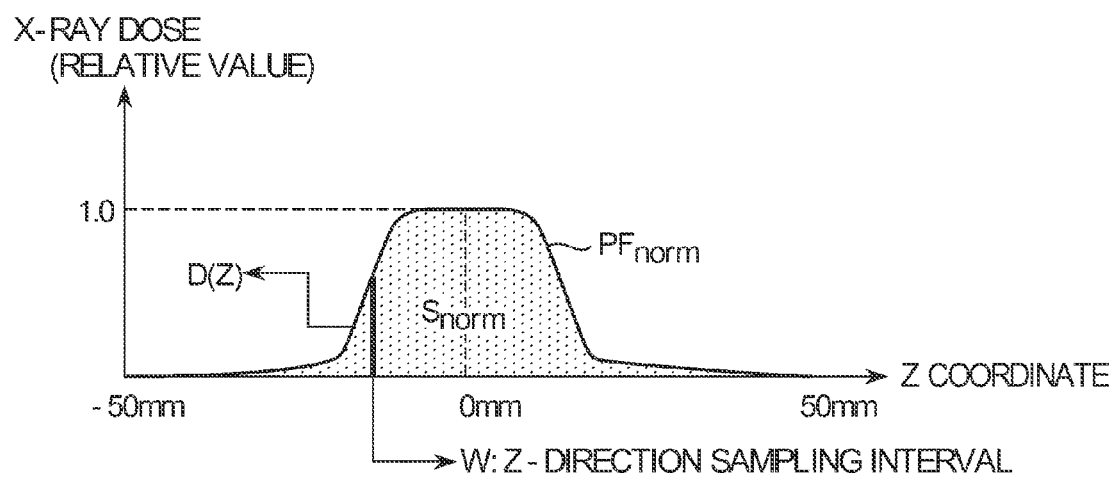
FIG. 9 schematically shows a method of normalizing a dose profile and finding a profile area.

When measured, the dose profile PF is normalized so that its peak dose value equals 1 as shown in FIG. 9. Normalized dose profile PFnorm is generated. The following equation is used to find profile area Snorm of the normalized dose profile PFnorm.

$$Snorm = \Sigma w \cdot D(Z) \qquad \text{Equation 5}$$

In this equation, w denotes the sampling interval (cm) in the z direction, and $D(Z)$ denotes the X-ray dose (relative value) along the Z-coordinate in the normalized dose profile PFnorm.

Figure 10:
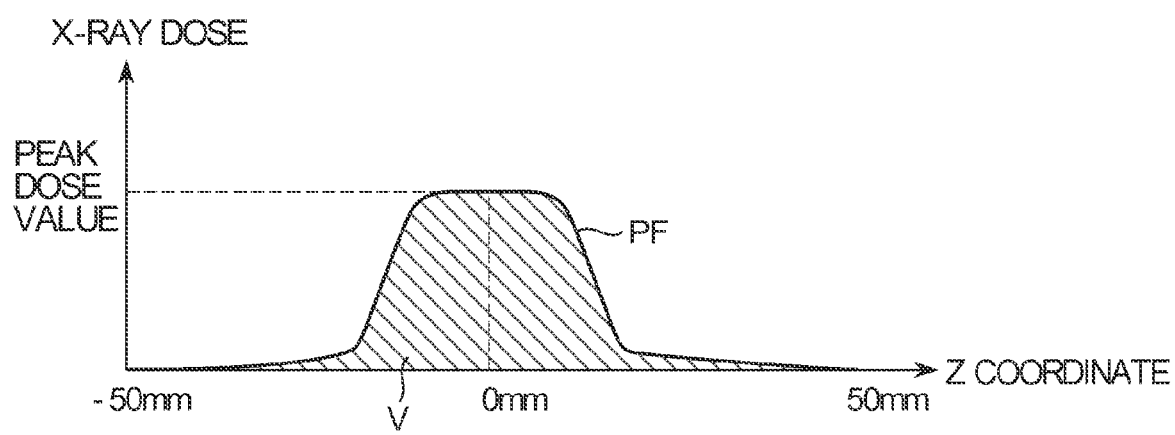
FIG. 10 shows a match between X-ray dose V and an area of dose profile PF.

The X-ray dose V measured above is equivalent to a value resulting from integrating X-ray doses belonging to the variance in the z direction. As shown in FIG. 10, the X-ray dose V corresponds to an area of the dose profile PF. It is supposed that ZPSD is the maximum dose (hereinafter referred to as a z-direction maximum surface dose) out of doses corresponding to the surface of the area reference phantom 50 in the z direction. Then, the following relationship is established.

$$ZPSD{:}V = 1{:}Snorm \qquad \text{Equation 6}$$

The X-ray dose V is divided by the profile area Snorm to find the z-direction maximum surface dose.

$$\text{Z-direction maximum surface dose } ZPSD = V/Snorm \qquad \text{Equation 7}$$

The embodiment assumes the z-direction maximum surface dose ZPSD to be the body surface reference dose skin_ref_Dose.

$$\text{Body surface reference dose skin\_ref\_Dose} = \text{z-direction maximum surface dose } ZPSD \qquad \text{Equation 8}$$

The second embodiment finds the body surface reference dose in consideration of the z-direction variance of doses near the surface of the reference phantom 50. Therefore, the embodiment can accurately find the value equivalent to body surface CTDI as the maximum of doses corresponding to the body surface.

Third Embodiment

Normally, a subject is placed on the cradle 12 of the scanning table 10. The X-ray passes through the cradle 12 and decreases the intensity. That is, the maximum dose is found on an upper surface of the subject where the X-ray is directly radiated before passing through the cradle 12.

FIG. 5 shows a type of scan, that is, a full scan that radiates the X-ray 81 around 360 degrees. The full scan is sure to radiate the X-ray 81 to the upper surface of the subject (the reference phantom 50 or the subject 40). In this case, the maximum dose is available near the upper surface of the subject and is independent of a view angle for starting the scan.

Figure 11:
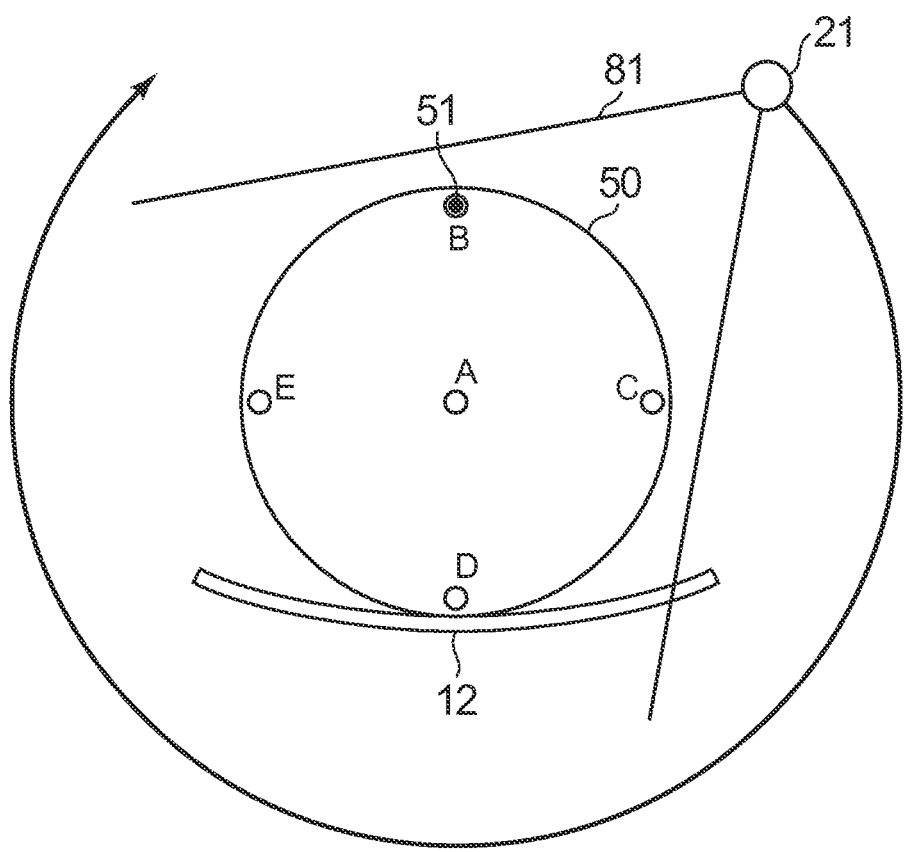
FIG. 11 illustrates virtual scan on a subject.

FIG. 11 shows another type of scan, that is, a partial scan that radiates the X-ray 81 around less than 360 degrees. For example, the partial scan includes half scan and segment scan. Depending on a range of view angles for scanning, the partial scan does not always radiate the X-ray 81 to the upper surface of the subject (the reference phantom 50 or the subject 40). In this case, the maximum dose near the surface of the subject depends on the range of view angles for scanning.

The embodiment finds a dose in consideration of the range of view angles for the type of scan that radiates the X-ray 81 around less than 360 degrees.

For example, the first embodiment is considered as a base. The scan type is assumed to be the full scan or the half scan. There are provided a body surface reference dose for the full scan and a body surface reference dose for the half scan.

The body surface reference dose for full scan is equivalent to an X-ray dose measured at the topmost measurement position of the reference phantom 50 when the full scan is performed on the reference phantom 50 under the scan condition of the reference dose ref_mAs as a dose (mAs).

On the other hand, the body surface reference dose for half scan is equivalent to an X-ray dose measured at the measurement position near the surface of the reference phantom 50 so as to maximize the dose when the half scan starts from a specified view angle and is performed on the reference phantom 50 under the scan condition of the reference dose ref_mAs as a dose (mAs). The position to maximize the dose may be theoretically found or actually measured at multiple positions. Multiple body surface reference doses for the half scan need to be found at view angles for starting the half scan.

The third embodiment finds and provides the body surface reference dose for the full scan and the multiple half-scan body surface reference doses found at view angles for starting the half scan corresponding to each of reference phantom types (sizes) and tube voltages.

The embodiment reads a body surface reference dose corresponding to the scan condition including the scan type, the tube voltage, the imaging portion, and the view angle for starting the scan. The embodiment then multiplies the body surface reference dose by the factor corresponding to the setup dose (mAs) to calculate a body surface dose.

The body surface reference dose for the half scan may be generated from averaging multiple X-ray doses measured at varied view angles for starting the half scan. This method is useful if a view angle for starting the scan is unknown or is omissible.

The third embodiment can find an appropriate body surface dose even though the scan type is enabled as the partial scan that radiates the X-ray around less than 360 degrees.

It is to be distinctly understood that the disclosure is not limited to the above-mentioned embodiments but may be otherwise variously embodied within the spirit and scope of the invention.

For example, the phantom used to find the reference dose is not limited to a columnar and acrylic reference phantom but may use other materials and shapes. Phantoms are not limited to two types, 16 cm and 32 cm in diameter, but may be available as the other sizes and three or more types.

For example, the method of measuring X-ray doses near the phantom surface is not limited to providing the X-ray sensor for the measurement position near the phantom surface and may provide the X-ray sensor so as to contact the phantom surface.

The above-mentioned embodiments assume the dose to be calculated and displayed as a CTDI value or its equivalent representing the dose per unit slice width or as a DLP value or its equivalent representing the dose for one whole examination. The dose may be calculated and displayed in terms of a value according to the other specifications.

The embodiments described herein are not limited to radiation tomography apparatuses represented by the X-ray CT scanner. An example embodiment may include a program allowing a computer included in the radiation tomography apparatus to function as the dose calculation portion 102 or a recording medium for storing the program.

What is claimed is:

1. A radiation tomography apparatus comprising:
   a calculator to calculate a dose near a surface of a subject based on a first radiation dose that results from dividing
   i) a radiation dose measured at a measurement position near a surface of a phantom when a scan of the phantom is performed by
   ii) a profile area resulting from normalizing a dose profile in a radiation beam width direction that corresponds to a body axis direction of the subject, the dose profile normalized according to a peak dose value of the dose profile,
   wherein the dose profile is measured at the measurement position when the phantom is irradiated with the same radiation beam width used for the scan; and
   a display controller to control a monitor to display the dose calculated by said calculator.

2. The radiation tomography apparatus according to claim 1, wherein
   the measurement position is a position where the radiation dose is substantially a maximum.

3. The radiation tomography apparatus according to claim 2, wherein
   the phantom is placed on a scanning table plate, and wherein the measurement position is a position most proximate to a radiation source.

4. The radiation tomography apparatus according to claim 1, wherein
   the dose profile results from averaging a plurality of dose profiles measured by positioning a radiation source for irradiation at a plurality of different view angles.

5. The radiation tomography apparatus according to claim 1, wherein
   said calculator is configured to calculate the dose based on a second radiation dose resulting from dividing the first radiation dose by a helical pitch of a helical scan when the helical scan is specified as a scan condition for the subject.

6. The radiation tomography apparatus according to claim 1, wherein
   said calculator is configured to calculate the dose based on a second radiation dose resulting from dividing the first radiation dose by a helical pitch equivalent according to a time-weighted average in a variable-pitch helical scan when the variable-pitch helical scan is specified as a scan condition for the subject.

7. The radiation tomography apparatus according to claim 1, wherein
   said calculator is configured to calculate the dose based on a view angle range for performing a partial scan that irradiates for less than 360 degrees, when the partial scan is specified as a scan condition for the subject.

8. The radiation tomography apparatus according to claim 1, wherein
   said calculator is configured to calculate the dose based on the first radiation dose obtained by performing a partial scan as the scan of the phantom, when the partial scan that irradiates for less than 360 degrees is specified as a scan condition for the subject.

9. The radiation tomography apparatus according to claim 1, wherein
   said calculator is configured to calculate the dose based on a second radiation dose resulting from averaging a plurality of the first radiation doses obtained by performing a partial scan for each of a plurality of view angle ranges different from each other as the scan of the phantom, when the partial scan that irradiates for less than 360 degrees is specified as a scan condition for the subject.

10. The radiation tomography apparatus according to claim 1, wherein
    a full scan that delivers radiation for 360 degrees is performed on the phantom.

11. The radiation tomography apparatus according to claim 1, wherein
    the phantom is acrylic and is shaped to be a column that is one of 16 centimeters and 32 centimeters in diameter, and wherein the measurement position has a depth in a range from 0.5 centimeters to 2.0 centimeters from the surface.

12. A dose calculation method comprising:
    measuring a radiation dose at a measurement position near a surface of a phantom when a scan of the phantom is performed;
    determining a profile area of a dose profile in a radiation beam width direction that corresponds to a body axis direction of a subject, the dose profile normalized according to a peak dose value of the dose profile at the measurement position, wherein the phantom is irradiated with the same radiation beam width as the scan; and
    calculating a dose for the subject imaged by a radiation tomography apparatus based on a first radiation dose resulting from dividing the radiation dose by the profile area.

13. A program configured to:
    instruct a computer to function as a calculator configured to calculate a dose near a surface of a subject based on a first radiation dose that results from dividing
    i) a radiation dose measured at a measurement position near a surface of a phantom when a scan of the phantom is performed by
    ii) a profile area resulting from normalizing a dose profile in a radiation beam width direction that corresponds to a body axis direction of the subject, the dose profile normalized according to a peak dose value of the dose profile,
    wherein the dose profile is measured at the measurement position when the phantom is irradiated with the same radiation beam width used for the scan; and
    instruct a display controller to control a monitor to display the calculated dose.

* * * * *